United States Patent [19]

Desrosiers

[11] Patent Number: 5,529,532
[45] Date of Patent: Jun. 25, 1996

[54] MINATURE MOTORIZED ANNULAR HAND HELD DENTAL SAW

[76] Inventor: Marc Desrosiers, 12,056 27th Avenue, Montreal, Quebec, Canada, H1E 1Z5

[21] Appl. No.: 507,777

[22] Filed: Jul. 26, 1995

[51] Int. Cl.⁶ .......................... B24B 23/00; B24B 27/08
[52] U.S. Cl. .................. 451/344; 30/276; 30/389
[58] Field of Search .................... 451/344, 523, 451/278; 30/276, 389

[56] References Cited

U.S. PATENT DOCUMENTS

| | | | |
|---|---|---|---|
| 2,972,363 | 2/1961 | Santilli | 143/44 |
| 3,461,557 | 8/1969 | Behring | 30/276 |
| 3,688,403 | 9/1972 | Bettcher | 30/276 |
| 3,799,021 | 3/1974 | Hammerschlag | 30/389 |
| 4,316,328 | 2/1982 | Duggan et al. | 30/389 |
| 4,363,170 | 12/1982 | McCullough | 30/276 |
| 4,472,880 | 9/1984 | Johansson | 30/389 |
| 4,494,311 | 1/1985 | McCullough | 30/276 |
| 4,575,938 | 3/1986 | McCullough | 30/276 |
| 4,637,140 | 1/1987 | Bettcher | 10/276 |
| 5,084,976 | 2/1992 | Ross | 30/276 |
| 5,230,154 | 7/1993 | Decker et al. | 30/276 |

FOREIGN PATENT DOCUMENTS 476783  4/1948  Canada.
759277  5/1967  Canada.

OTHER PUBLICATIONS

Disclosure Document (335505): Miniature annular hand held dental saw.

*Primary Examiner*—Bruce M. Kisliuk
*Assistant Examiner*—Derris Banks

[57] ABSTRACT

A miniature motorized hand held dental saw wherein, like with a coping saw, the axis of rotation of the handle of the dental saw is tangent with the outer diameter of the blade. This important characteristic, combined with the use of a flexible blade, enables the operator to change, as needed, the direction of the cut without any snagging or binding effects. The dental saw is composed of a main steel body on which are attached three flanged Teflon™ coated bearings that support and guide a 0.004 thick annular diamond coated blade. The rotation of the blade, on these flanged bearings, is created by a drive assembly consisting of two opposite wheels, a drive wheel and a follower wheel, each wheel composed of a hub on which is fitted a neoprene o-ring. The opposite o-rings create an equal pressure on both faces of the blade which they make rotate. The power is transmitted to the assembly by means of a drive cable that is connected to a motor situated in a remote stationary work station.

13 Claims, 7 Drawing Sheets

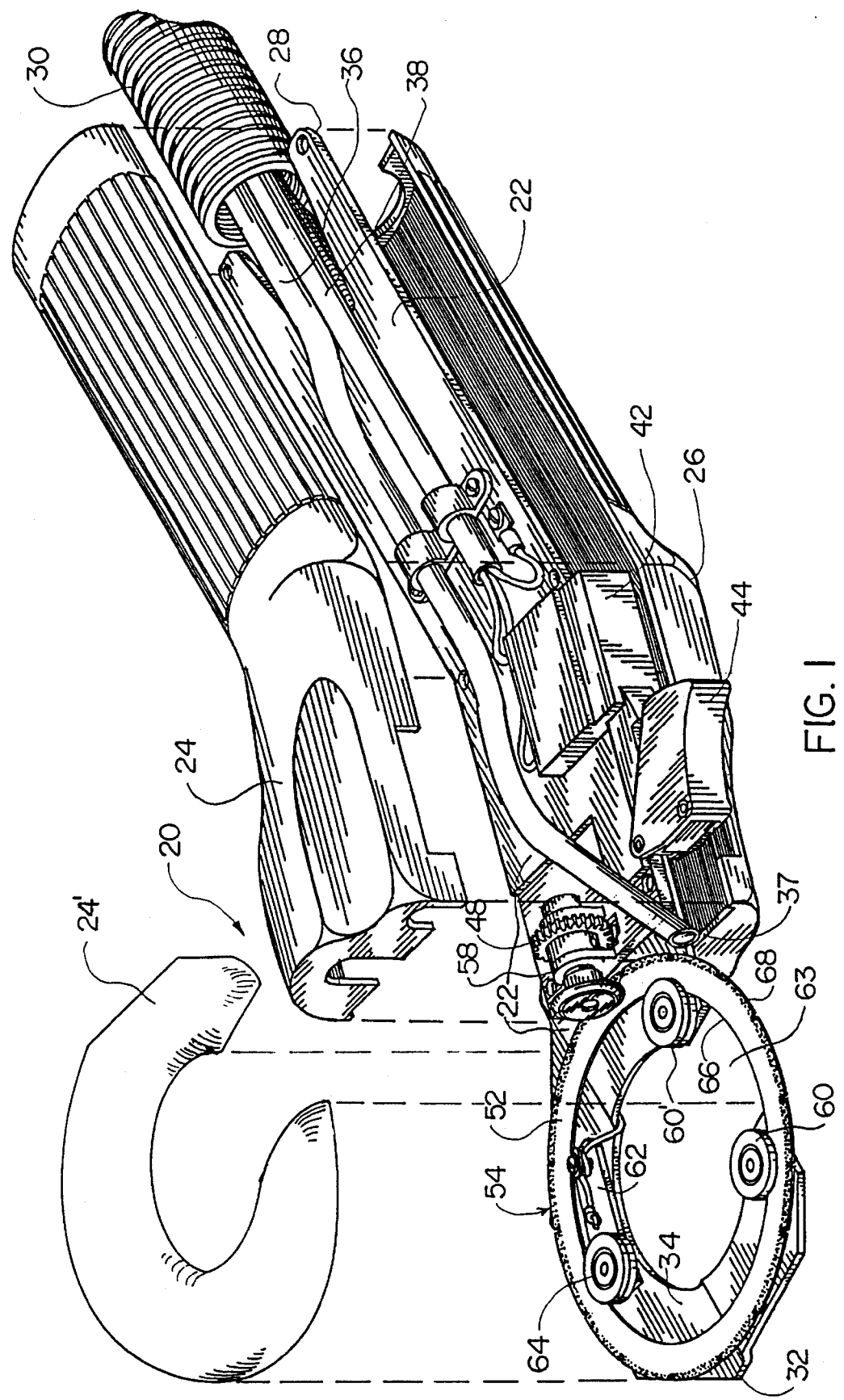
FIG. I

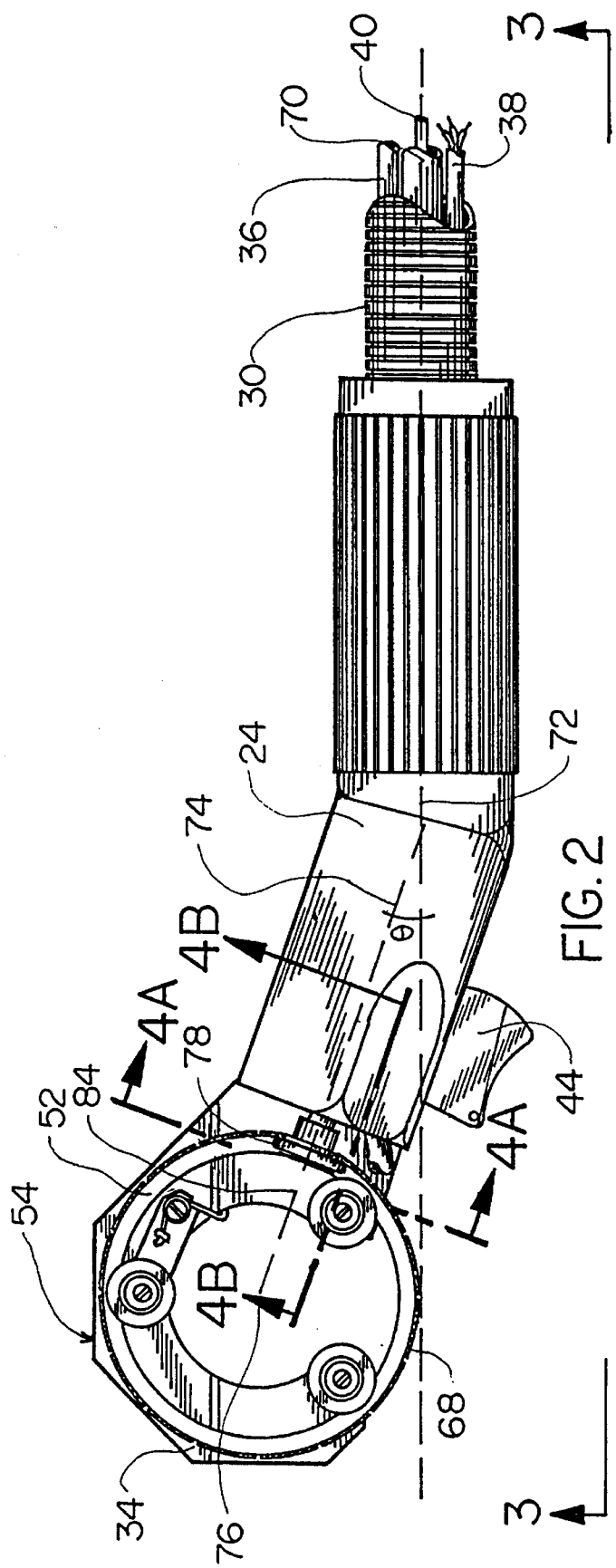
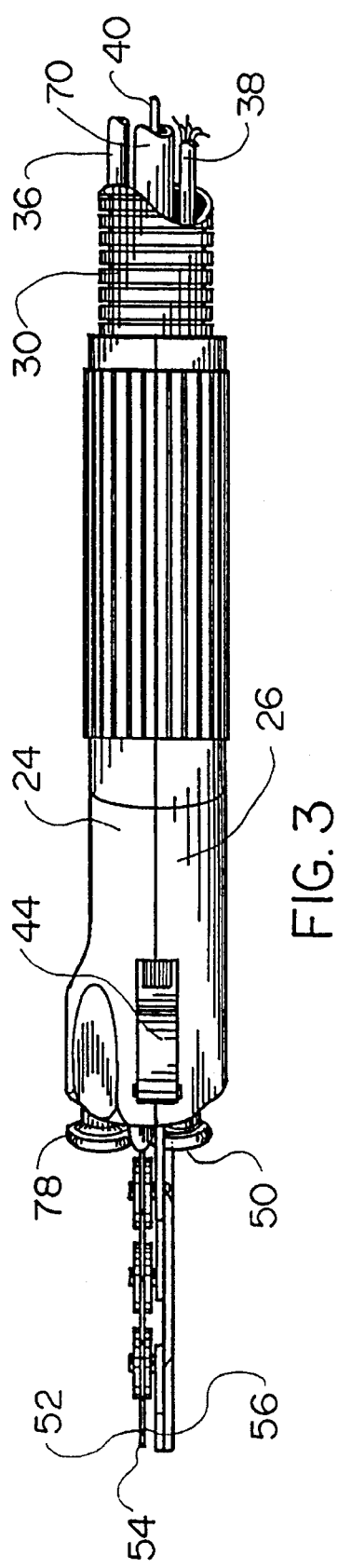

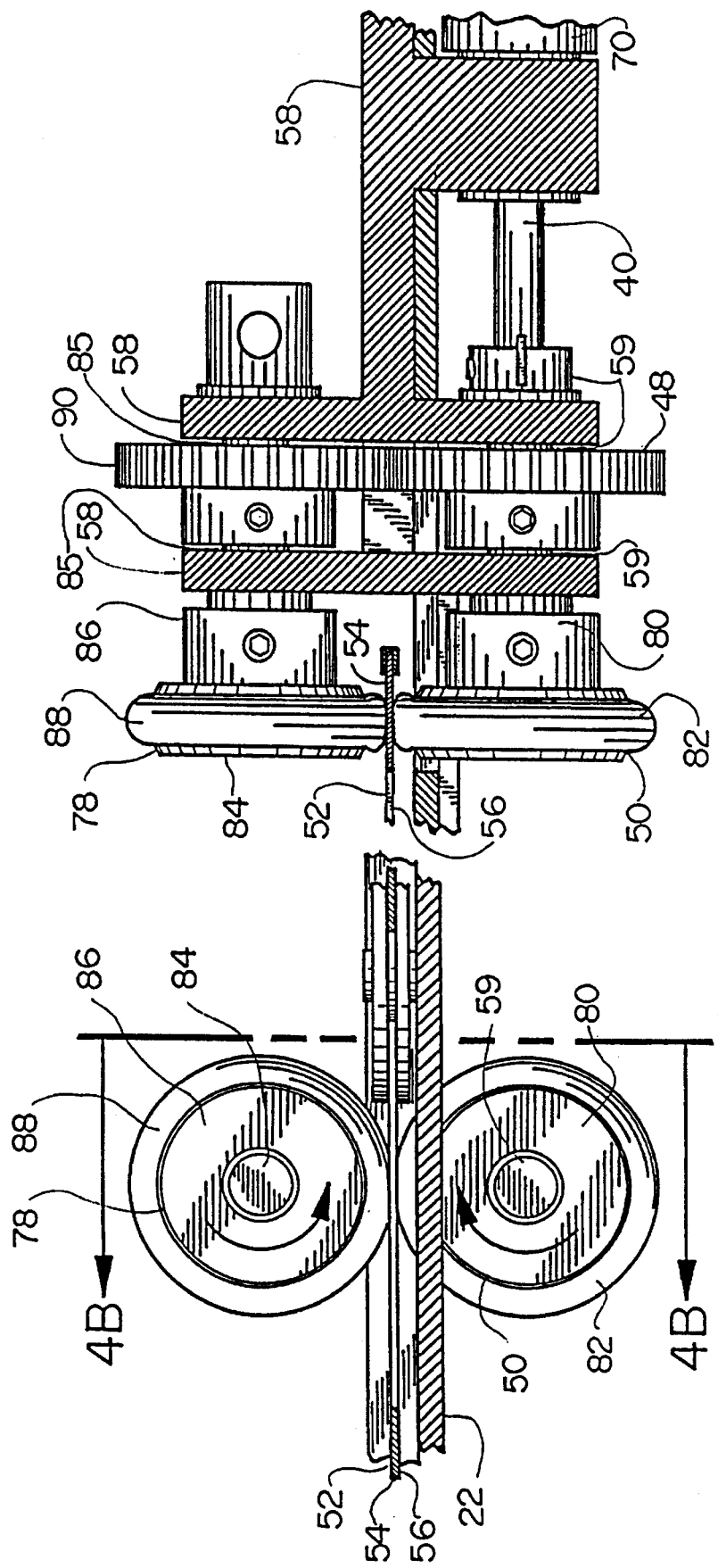

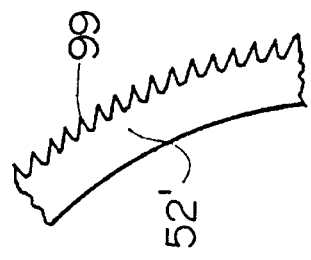
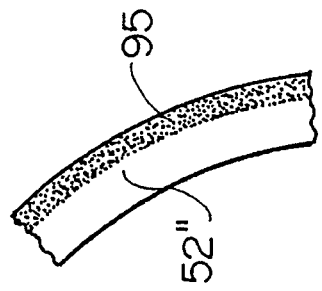
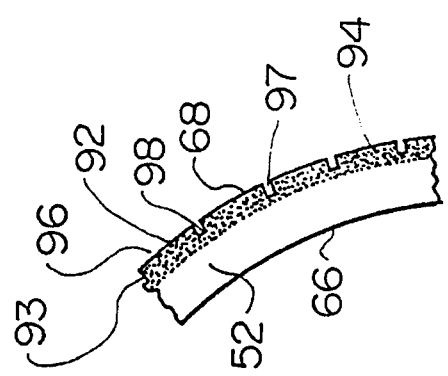
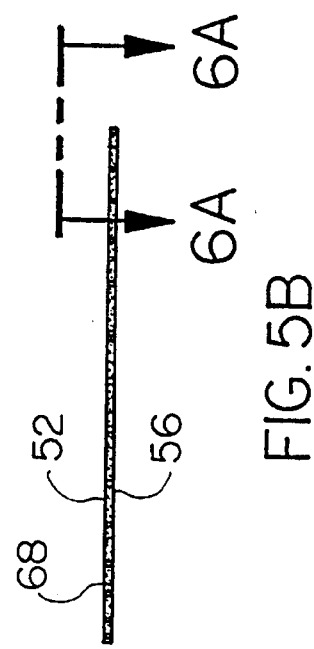
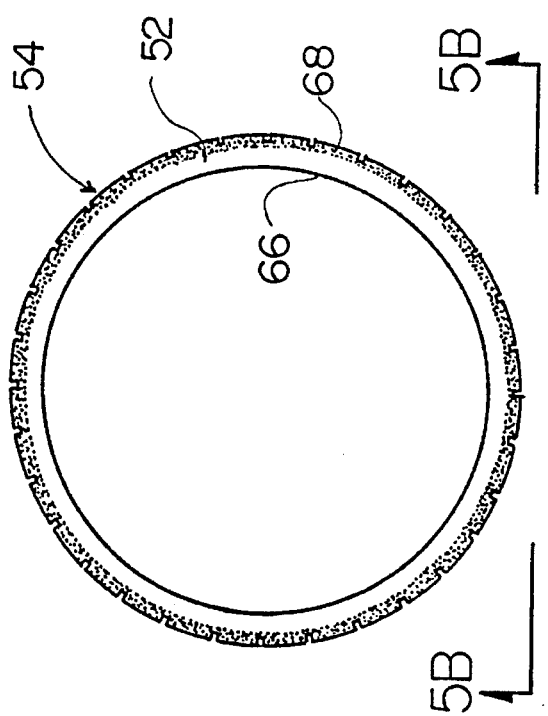

MINATURE MOTORIZED ANNULAR HAND HELD DENTAL SAW

BACKGROUND-FIELD OF THE INVENTION

This invention belongs to the field of dental preparation and specifically to the field of the preparation of models in a dental laboratory. This invention is for an apparatus that is used to separate individual teeth referred to as dies used in dental techniques. Dies are separated from complete upper or lower models. Such models are made of plaster, artficial stones and plastic or epoxy materials.

Prior Art

The initial idea was to develop a motorized saw which operated very much like a band saw mounted in a horizontal position. From this point the biggest difficulty would be to locate or develop a band type blade whose thickness would be less than 0.007 inches. The thin blade was essential due to the small size of the dental dies and to obtain the thinnest cut possible. The band saw idea was dropped and replaced by a hollow blade or a rim saw which could provide dental technicians with a motorized saw that would perform the same operation as a traditional coping saw.

A patent search revealed that a patent for a mechanical saw with a rimless blade already existed in the forest industry (1945): the review of the prior art revealed certain patents having a connection with some annular saws which perform certain operations. The following patents have retained my attention.

CN 476783 Fortier, 13 Apr. 1948 shows an annular blade for cutting an object such as a tree whose diameter is larger than the radius of the annular blade. The blade is commanded by gear teeth acting upon the annular surface of the blade, with the steel teeth engaging steel openings. The blade has been used in lumber cutting with, as a result, the dragging of wood chips between the gear teeth and the walls of the openings; the blade had to be hard and not flexible.

U.S. Pat. No. 4,472,880 Johansson, 25 Sep. 1984, shows two steel wheel drive rollers 25, 26 forming wedge shaped grooves 40 to facilitate the contact of the steel rollers against the blade. The inner bevels help in the guiding of the blade during rotation but account for a wider cut, which is satisfactory in cement or granite cutting with water but not for fine cutting used without water in dentistry.

U.S. Pat. No. 2,972,363 Santilli, 21 Feb. 1961. The command system is a round gear 26 meshing into hole 25 on the face of the blade. A roller 13 has a number of such gears 26. Friction is excessive as friction is applied iron to iron and directly from a motor, without easy adjustment of the speed of the motor.

None of the known methods disclosed an apparatus which is a motorized annular saw designed to duplicate the motion of a hand held-coping saw, which is widely used around the world, while allowing as much control on the tilting of the tool during cutting, as when using the manual coping saw, and while permitting increased speed, maneuverability and longer lasting blades.

OBJECTIVE OF THE INVENTION

A general objective of the present invention is to provide a motorized saw and blade for the fine cutting of plaster models such as for dental plaster dies, for example for the fabrication of crowns and bridges in dental techniques and wherein the axis of rotation of the handle is tangent with the tip of the teeth of the blade, or with the external diameter of a diamond lined blade, the blade being flexible, to allow the operator to modify the course of the cut, thus permitting the blade to change direction during the cut.

SUMMARY OF THE INVENTION

To provide an annular flexible saw blade having a thickness, a diameter, two opposite flat faces, an inner edge, an outer edge and a 304 stainless steel fully hardenend composition, and comprising in combination:

cutting teeth formed at the outer edge thereof, the cutting teeth to comprise diamond particles incorporated into the outer edge, the diamond particles being of a size ranging from 140 to 400 mesh.

the outer edge to comprise segments covered by diamond particles each segment defining a rectangle with two long sides and two short sides, each long side being in length equivalent to 30° or less around the circumference, and each short side comprising an open area, with an indent taking the form of an open square of sides equal to half the width of the short side.

the diameter comprising an outside diameter at the outer edge and an inside diameter at the inner edge, the flat faces having a width corresponding to half of the difference between the outside diameter and the inside diameter, the inside diameter being no less than 75% of the outside diameter and no more than 97% of the outside diameter, the thickness relative to the diameter being in a ratio varying from 0.5 to 1000, to 3 to 1000.

To provide a power operated saw machine for cutting materials comprising in combination:

a main body having a fore end and an aft end, a rotating axis and being capable of being oriented about the rotating axis, an annular cutting blade comprising an outer edge, a first flat face and a second flat face opposite to the first flat face, and an inner edge, the outer edge corresponding to a perimeter and comprising cutting means disposed along the perimeter, the annular cutting blade being mounted by mounting means on the fore end of the main body, the mounted position of the annular cutting blade being such that a tangent to the perimeter coincides with an extension of the rotating axis of the main body, means for engaging the annular cutting blade into a rotation against the materials, the cutting means dislodging the materials along the tangent, in the direction of the rotating axis, so that any torsional movement of 1° of the main body around the rotating axis causes the same torsional movement of 1° at the perimeter of the annular cutting blade. A power source is remote and flexibly conducted to the saw machine. The power source is an electric motor connected to a torsion cable mounted in a flexible sheath and coupled to the means for engaging. The means for engaging comprise two friction wheels mounted against the opposite first and second flat faces, a first friction wheel driven by the torsion cable, to turn at the same angular speed as the torsion cable, a second and opposite friction wheel concentrically mounted to a follower device maintained in motion by a command device turned by the torsion cable, the follower device and the command device turning at same angular speed.

The means for mounting the blade comprise a set of three flanged guide bearings in contact against the inner edge, two of the flanged guide bearings having each a fixed central axis and having between each other a cutting area to permit passage of a piece to work on, the third flanged guide bearing being mounted on a spring arm located on the fore end and being biased towards the inner edge. The means for control of the electric motor comprise a conduit and a pressure switch to apply various speeds.

To provide an annular cutting blade engaged into rotation by a command wheel centrally mounted on the drive cable and peripherally exerting a friction drive against the flat face, the drive cable also engaging a command gear meshing with a follower gear of identical diameter, the follower gear driving a follower wheel acting on the second flat face of the annular cutting blade and in transverse register with the command wheel relative to the cutting blade.

DESCRIPTION OF THE DRAWINGS

I will describe more in details hereinafter by way of an indication, nonetheless limitative, an apparatus true to the present invention in reference to the annexed drawing on which:

FIG. 1 is a perspective view of a miniature annular hand held dental saw system with outer shells removed, along dotted lines.

FIG. 2 is a front view of the system of FIG. 1, seen from the left side and with a partial cut.

FIG. 3 is a bottom view according to line 3—3 of FIG. 2.

FIG. 4A is a cut view according to line A—A of FIG. 2.

FIG. 4B is a cut view according to line B—B of FIG. 2.

FIG. 5A is a top view in the region of arrow 54 of FIG. 1.

FIG. 5B is a front view according to line 5B—5B of FIG. 5A.

FIG. 6A is a detailed top view according to line 6A—6A of FIG. 5B.

FIG. 6B is a view such as that of FIG. 6A illustrating a first alternative.

FIG. 6C is a view such as that of FIG. 6A illustrating a second alternative.

DESCRIPTION OF A PREFERRED EMBODIMENT

Figure 7A:
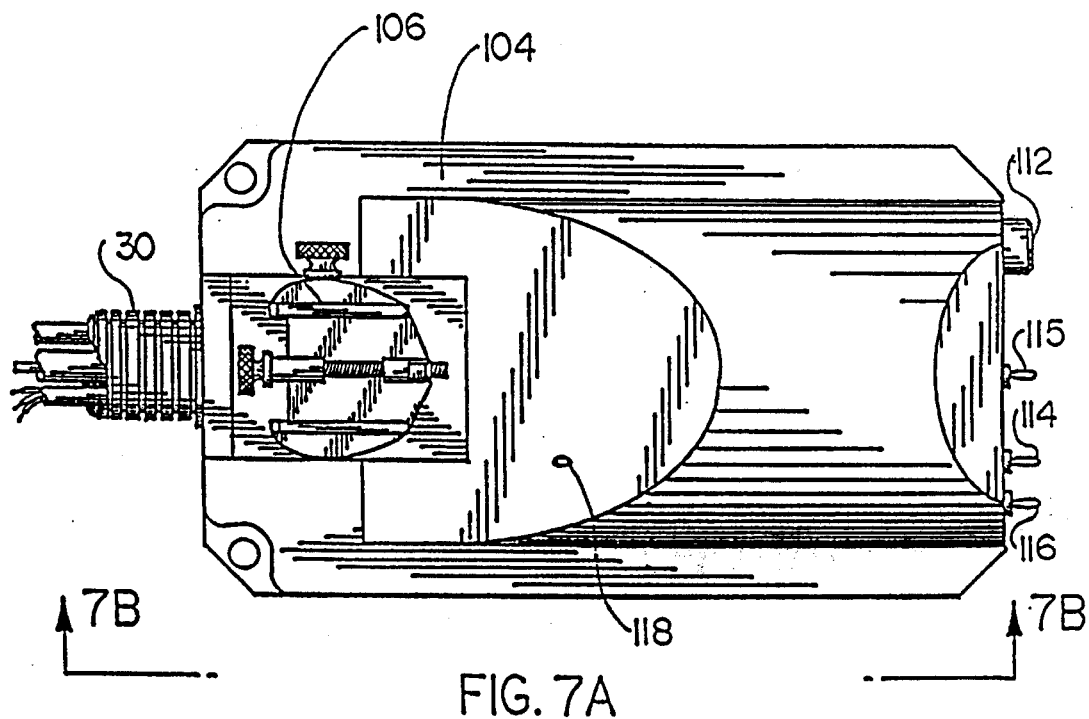
FIG. 7A is a top view showing a work station.

An embodiment of the invention is described in the following figures where the same characterizing elements are identified by the same numbers and where one sees: at FIG. 1, a miniature annular hand held dental saw 20 comprising a main body 22 assembled to an outer shell, left 24 and to an outer shell, right 26, by what appears to be dotted lines. The main body 22 holds, at an aft end 28, a conduit 30 and, at a fore end 32, an arked support 34. The conduit 30 surrounds a vacuum tube 36 with an aspiration opening 37, an electrical cable 38 and a drive cable 40, which appears in Fig.2. The electrical cable 38 leads to a variable speed control 42 equipped with a finger plunger 44, to transmit a signal to a motor 46 (FIG.7) which commands the drive cable 40, and which leads rotative power to a command nylon gear 48 (FIG.4B) which coaxially transmits power to a command wheel 50 which engages a right face 56 of an annular diamond flexible blade 54. A drive assembly 58 supports a coaxial shaft 59 which transmits power from the command nylon gear 48 to the command wheel 50.

The arked support 34 (FIG. 1) sustains two fixed flanged guide bearings 60 separated by a cutting area 63 and a third flanged guide bearing 64 fixed to a mobile spring loaded tension arm 62. The two fixed flanged guide bearings 60 and the third flanged guide bearing 64 touch at three points an inner edge 66 corresponding to the inside diameter of the annular diamond flexible blade 54, while an outer edge 68 corresponding to the exterior diameter is free to work.

At FIG. 2, one can see a view of the outer shell, left 24, assembled over the outer shell, right 26 (FIG.3) and with the finger plunger 44 in position ready to be actionned for controlling the traction of command wheel 50 over the right face 56. One sees the drive cable 40 in a sheath 70 both oriented at the onset in conduit 30 along a handle rotation axis 72 (FIG. 2), and further along at the outset when in a geometric plane 74 passing through both the axes of the coaxial shaft 59 of the command wheel 50 and a follower axis 84 of a follower wheel 78, the geometric plane 74 continuing to the center 76 of the annular flexible diamond blade 54, the junction between the geometric plane 74 and the handle rotation axis 72 forming an angle Ø. For best results it is desirable that the angle Ø be such that the continuation of the handle rotation axis 72 coincide with a tangent of a circle formed by the outer edge 68 of the annular diamond flexible blade 54.

At FIG. 3, one can see the command wheel 50 acting against the right face 56 of the annular diamond flexible blade 54 being supplemented by the follower wheel 78 acting against the left face 52. The vacuum tube 36 and the electrical cable 38 appear in the same relative position with respect to the sheath 70.

At FIG. 4A, one can see the command wheel 50 turning clockwise with the coaxial shaft 59, the command wheel 50 comprising two parts, namely a command brass hub 80 and a neoprene drive o-ring 82 which surrounds the command brass hub 80. It is the neoprene drive o-ring 82 which is adapted to rest against the right face 56. The direction of rotation of the drive wheel 50 is shown clockwise. Facing the drive wheel 50 is a follower wheel 78 with follower axis 84 and a follower brass hub 86 surrounded by a neoprene follower o-ring 88 which frictionnally engages the left face 52 of the annular diamond flexible blade 54.

At FIG. 4B, one can see the drive cable 40 command the command nylon gear 48 and at the same time rotate the coaxial shaft 59 which engages the command wheel 50 and the neoprene drive o-ring 82 which frictionnally engages the right face 56. The command nylon gear 48 engages a similar follower nylon gear 90 which turns a follower shaft 85 which turns the follower wheel 78 and the neoprene follower o-ring 88, which also frictionnally engages the left face 52 of the annular diamond flexible blade 54 in a counterclockwise direction.

At FIG. 5A one can see the annular diamond flexible blade 54 having a thickness, a diameter, flat left and right faces 52, 56, an inner edge 66, an outer edge 68 and a flexible material composition:

the preferred flexible material composition is of type 304 stainless steel fully hardened;

cutting teeth are formed at the outer edge 68 and may be of three possible types;

the flat faces when seen on edge have a left side and a right side, both sides being adapted to be frictionnaly engaged: the rate of turning is high namely of the order of 5000 r/m, which increases the pressure of the o-ring against the flat face of the blade by the centrifugal force: two rubber rings are preferably used, one on each side;

the inner edge 66 may be held by a number of flanged bearings which simply support and maintain the blade in a relatively stable position while turning around an imaginary central axis: the turning flanged bearings have a reentrant part resting against the inside diameter of the inner edge 66 and two flanges touching the left face 52 and right face 56: the area touching the faces and the edges are preferably lined with Teflon™. It is also possible in another embodiment to use a toothed inner edge with a set of three engaging and idle sprockets causing the inner edge to turn;

the thickness relative to the diameter is of a ratio varying from 0.5 to 1000, to 3 to 1000, a typical thickness of an annular diamond flexible blade being 0.004" and the diameter being 3.00", the diameter comprises an outside diameter at the outer edge 68 and an inside diameter at the inner edge 66, the flat face having a width corresponding to half of the difference between the outside diameter and the inside diameter, the inside diameter being no less than 75% of the outside diameter and no more than 95% of the outside diameter.

A section of the blade with diamond particles 95 is illustrated in FIG. 6B, the desirable particle size being 230/270 mesh in a matrix of nickel. A segmented design is preferable, such as shows in FIG. 6A, for increased cutting rates. Each rectangular segment comprises a long side 92 placed tangentially to the outer edge 68, a short side 93 placed radially, a leading edge 96 and a trailing edge 98. The trailing edge 98 shows an opening 97 of square shape, the length of the square side being half of the rectangular segment short side 93. The cutting operation produces dust which tends to deposit on both faces of the blade; with an opening 97 between two segments 94, any dust generated during cutting tends to concentrate in the open trailing edge 98 rather than on the faces of the blade which would cause a wider cut. With the trailing edge opening 97, the dust collects in the opening 97 and goes out in bursts, to be aspirated by the aspiration opening 37. A number of 32 segments 94 is recommended.

At FIG. 6C one can see a cut piece of an annular flexible blade carrying saw teeth 99.

At FIG. 7A one can see a work station 104 and a survey model table 106, a vacuum outlet 112, a hand/foot optional selector switch 114, a foot switch connector 115, an on/off power switch 116 and an on/off light switch 118.

Figure 7B:
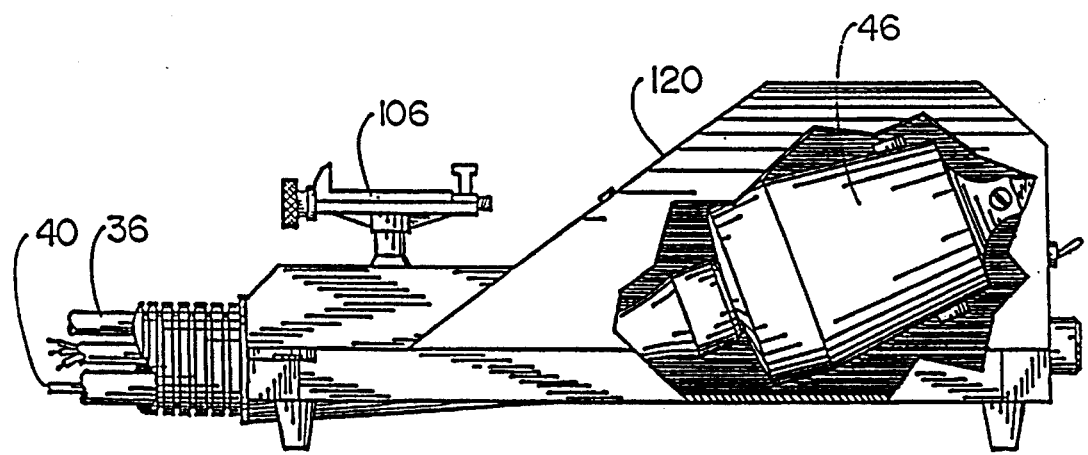
FIG. 7B is a front view according to line 7B—7B of FIG. 7A.

At FIG. 7B a motor 46 and a fire retardent plastic cover 120.

Figure 8:
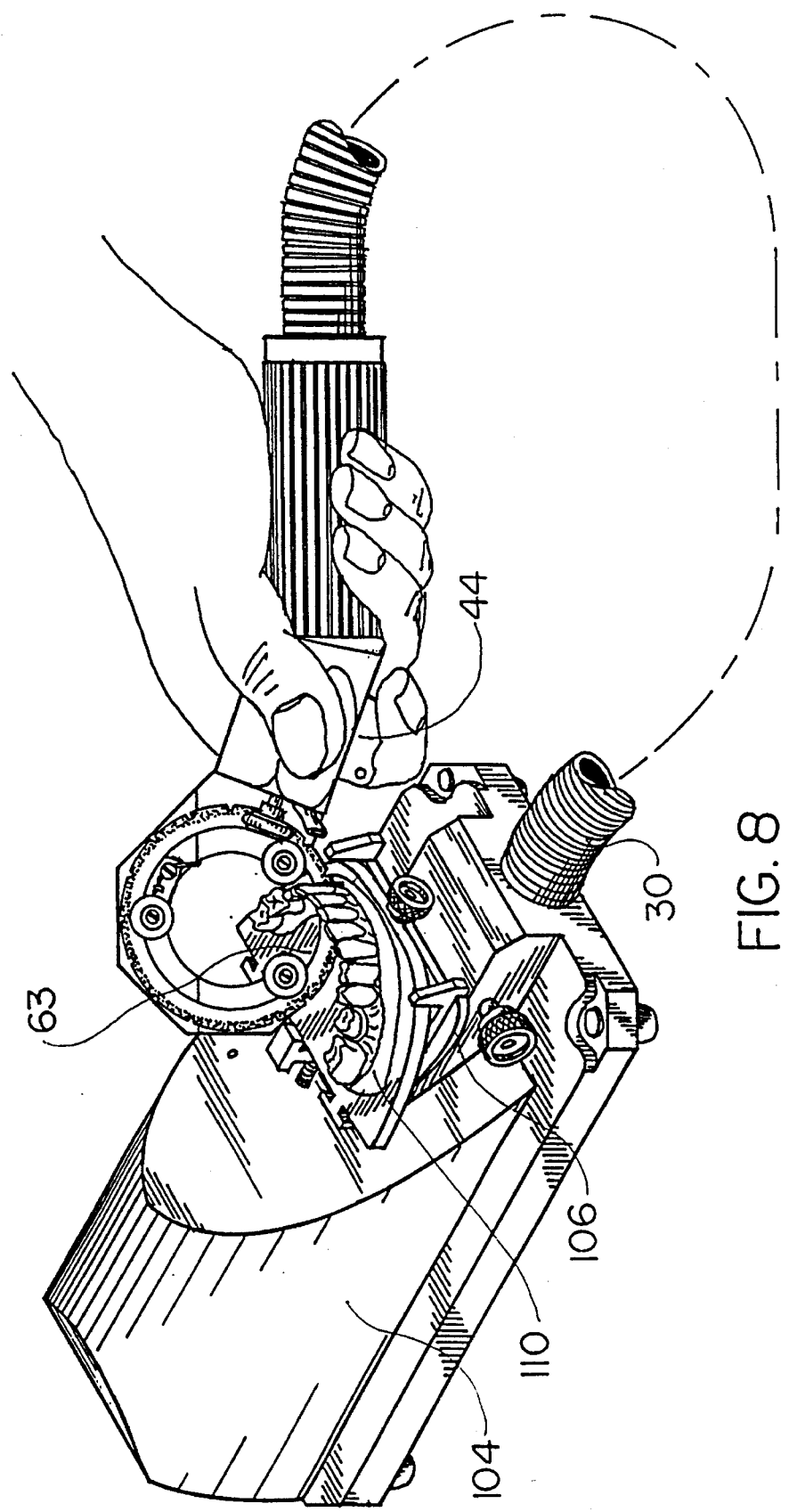
FIG. 8 is a perspective illustrating a cutting operation.

At FIG. 8 one can see the work station 104, the survey model table 106 and a model 109 on which can be observed the separating of a die 110 being worked on utilising cutting area 63.

Figure 9A:
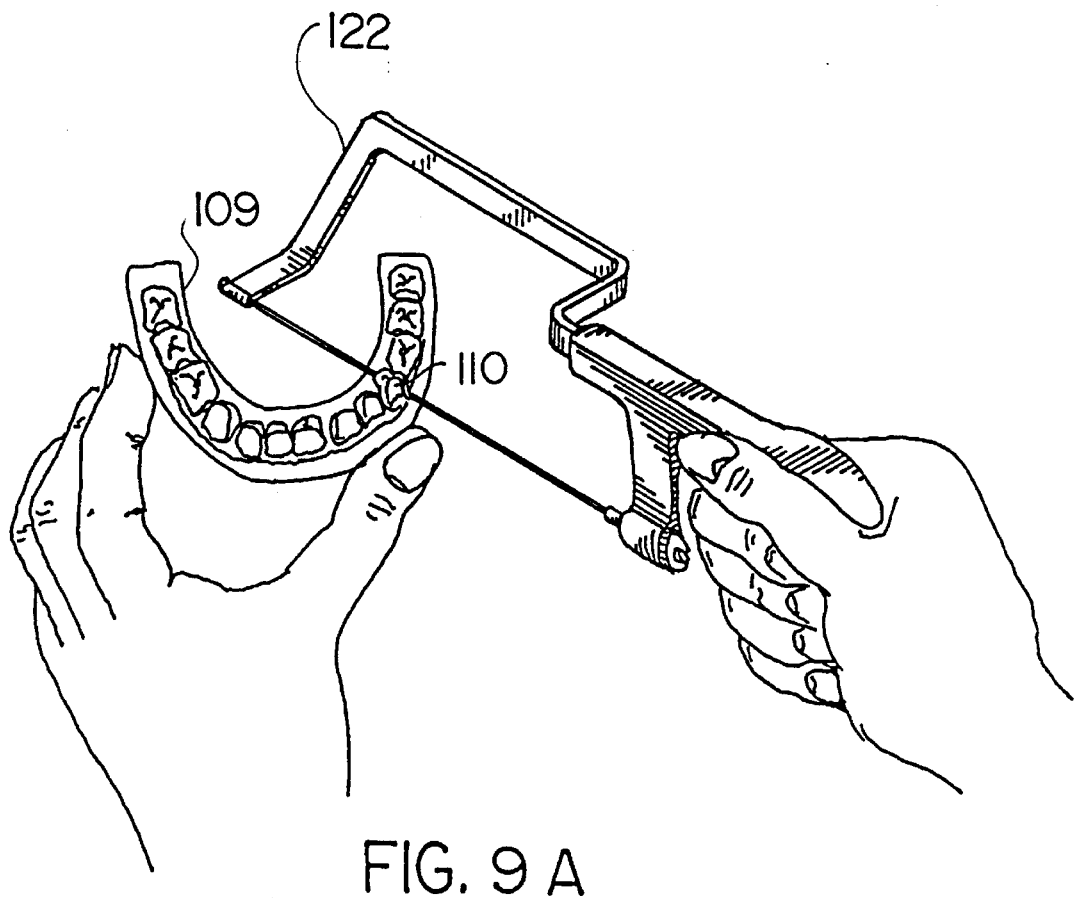
FIG. 9A is a view of prior art illustrating a cutting operation with a coping saw.

At FIG. 9A, one can see a view of prior art, a model 109 is shown being held by a hand, showing the separating of a die 110 with a traditional coping saw.

Figure 9B:
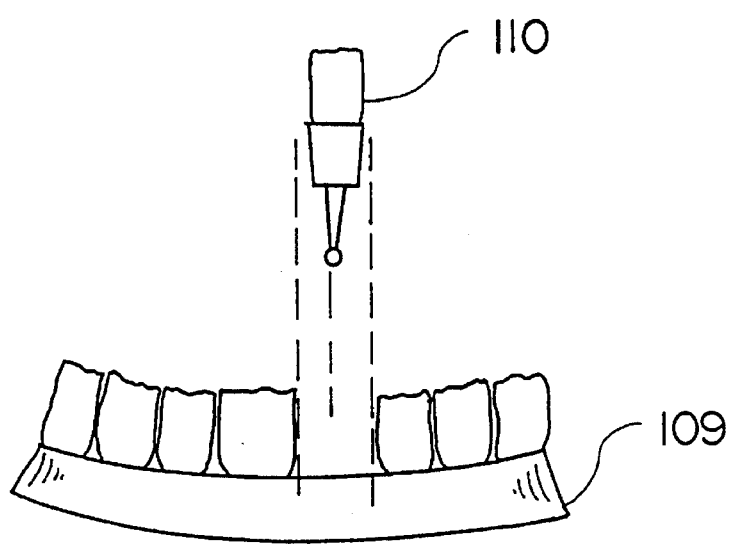
FIG. 9B is a view of a model with the die extracted.

At FIG. 9B one can see a die 110 extracted from the model 109 once the cuts have been made on each side.

MODE OF OPERATION

The first step is to identify the structure surrounding the cut to be made by the "Die Ripper"™ flexible annular saw. In dentistry: a model is held on a work table. In the case of a surgical tool, the part to be cut may be especially positionned: for example, mechanical saws are still used in most amputations which take place in North America and abroad. If attempting to use the flexible annular saw for new type of operations, one must take into account the size of the cutting area between the two flanged guide bearings, as well as the overall size of the saw blade.

In dentistry the following steps are accomplished:

Place model on survey table

Grab Die Ripper™ in hand and place the cutting area above the proposed die to be separated.

Slowly depress the finger plunger thus controling the cutting speed: once the cut is commenced increase or decrease the speed to finalize the cut. The operator can start the cut from the top towards the bottom, as would be done with a coping saw, and he can also change direction of the cut when nedeed because of the flexibility of the blade. The dust produced by the cutting action is sucked away by the aspiration opening 37 which is connected to a vacuum outlet 112 existing system in the laboratory. The operator may choose either a toothed blade (0.006 inch width) or a diamond coated blade (0.004 inch width)

Technological advancements

A useful feature of the annular diamond flexible blade held by the saw is its ability to reproduce at near 100% success rate a function which can only be performed by a manual coping saw at the present time: the motorized annular saw will allow the operator to change the direction during the cutting function. Known motorized saws do not permit the operator to perform this function.

In addition, most motorized saws are limited to a fixed direction of cut; the operator must first align the die at the right angle before proceeding with the desired cut. Once this is performed the operator then either brings the die up to the cutting blade or vice-versa to perform the first task.

The deficiency of the present motorized saws are evident when an operator attempts to perform a second cut which must be aligned either parallel or inverted taper with the first cut. This task becomes very difficult, time consuming and lacks precision. The only alternative which is presently available to the operator is to return to the hand held coping saw in order to attain the desired level of precision and/or finish the cut.

The "Die Ripper"™ corrects this deficiency for many reasons. Firstly, greater maneuverability is achieved since it is not fixed. Secondly, the variable speed which is available permits the operator to start the cut slowly with great precision during the more difficult and delicate initial cut and to then speed up to complete the cut: thirdly, it completely eliminates the need for the use of the hand held coping saw. The entraining wheels, the command wheel 50 and the follower wheel 78, are localized at a certain distance from the work zone to permit a bending of the blade to occur during the cutting operation, as the cutting part of the blade is remote from the zone of the application of friction by the wheels 50 and 78.

Another major deficiency with present fixed motorized blades is the fact that some of the models have a high level of vibration. This causes the cuts to lack precision, but more importantly, it often causes the die itself to crack or break. If this happens, the whole process must be started again whereby a new die must be prepared by making a new imprint of the client's teeth. The "Die Ripper"™ alleviates this problem since the vibration will be negligible and by the fact that the operator can adjust the speed of the operation, depending on the level of difficulty and precision which is associated with the cut. The "Die Ripper"™ will also introduce a new level of precision to the cutting process because of the thinness of the blades. The thinner blade will cause the operator to achieve a higher level of precision, will minimize the vibration and will also lower the risk of damaging the dental imprint reproduction.

It is well understood that other embodiments of the present invention, in reference to the annexed drawing may be constructed with other modifications and adaptations limited only by the scope of the following claims:

Parts list

| | | | |
|---|---|---|---|
| 20 | dental saw | 70 | sheath |
| 22 | main body | 72 | handle rotation axis |
| 24 | outer shell, left | 74 | geometric plane |
| 26 | outer shell, right | 76 | center |
| 28 | aft end | 78 | follower wheel |
| 30 | conduit | 80 | command brass hub |
| 32 | fore end | 82 | neoprene drive o-ring |
| 34 | arked support | 84 | follower axis |
| 36 | vacuum tube | 85 | follower shaft |
| 37 | aspiration opening | 86 | follower brass hub |
| 38 | electrical cable | 88 | neoprene follower o-ring |
| 40 | drive cable | 90 | follower nylon gear |
| 42 | variable speed control | 92 | long side  93  short side |
| 44 | finger plunger | 94 | segment |
| 46 | motor | 95 | diamond particles |
| 48 | command nylon gear | 96 | leading edge |
| 50 | command wheel | 97 | opening |
| 52 | left face | 98 | trailing edge |
| 54 | annular diamond flexible blade | 99 | saw teeth |
| | | 104 | work station |
| | | 106 | survey model table |
| 56 | right face | 109 | model    110  die |
| 58 | drive assembly | 112 | vacuum outlet |
| 59 | coaxial shaft | 114 | selector switch |
| 60 | flanged guide bearings | 115 | foot switch connector |
| 62 | spring loaded tension arm | 116 | on/off power switch |
| 63 | cutting area | 118 | on/off lightswitch |
| 64 | third flanged guide bearing | 120 | plastic cover |
| 66 | inner edge   68  outer edge | 122 | coping saw |

I claim:

1. An annular flexible saw blade having a thickness, a diameter, two opposite flat faces, an inner edge, an outer edge and a stainless steel composition, said annular flexible saw blade comprising in combination:

said two opposite flat faces having cutting teeth formed at the outer edge thereof, said diameter comprising an outside diameter at said outer edge and an inside diameter at said inner edge, said flat faces having a width corresponding to half of the difference between said outside diameter and said inside diameter, said inside diameter being no less than 75% of said outside diameter and no more than 97% of said outside diameter, said thickness relative to said diameter being in a ratio varying from 0.5 to 1 000, to 3 to 1 000.

2. An annular flexible saw blade as defined in claim 1 wherein said stainless steel composition is type 304 fully hardened.

3. An annular flexible saw blade as defined in claim 2 where said cutting teeth comprise diamond particles 95 incorporated into said outer edge substantially around the perimeter of said annular blade.

4. An annular flexible saw blade as defined in claim 3 wherein said diamond particles 95 are of a size ranging from 140 to 400 mesh.

5. An annular flexible saw blade as defined in claim 4 further comprising segments covered by said diamond particles 95, each segment defining a rectangle with two long sides and two short sides, each long side being in length equivalent to 30° or less around the circumference, and each short side providing an open area.

6. An annular flexible saw blade as defined in claim 5 wherein said open area takes the form of an open square of sides equal to half the width of said short side.

7. A power operated saw machine for cutting materials through a solid element, said power operated saw machine comprising in combination:

a main body 22 having a force end and an aft end, a rotating axis 72 and being capable of being oriented about said rotating axis, an annular cutting blade 54 comprising an outer edge, a first flat face and a second flat face opposite to said first flat face, and an inner edge, said outer edge corresponding to a perimeter, said annular cutting blade 54 being mounted by mounting means on said force end of said main body, the mounted position of said annular cutting blade 54 being such that a tangent to said perimeter coincides with an extension of said rotating axis of said main body, means for engaging said annular cutting blade into a rotation against said solid element, said cutting means dislodging said materials along said perimeter and along said tangent in the direction of said rotating axis, so that any torsional movement of 1 degree of said main body 22 around said rotating axis causes the same torsional movement of 1 degree at said perimeter of said annular cutting blade, said cutting means having a diameter and a thickness, wherein said diameter comprising an outside diameter at said outer edge and an inside diameter at said inner edge, said flat faces having a width corresponding to half of the difference between said inside diameter being no less than 75% of said outside diameter and no more than 97% of said outside diameter, said thickness relative to said diameter being in a ratio varying from 0.5 to 1 000, to 3 to 1 000.

8. A power operated saw as defined in claim 7 wherein said means for power operation comprise a remote power source flexibly conducted to said saw machine.

9. A power operated saw as defined in claim 8 wherein said power source is an electric motor connected to a torsion cable mounted in a flexible sheath and coupled to said means for engaging.

10. A power operated saw as defined in claim 9 wherein said means for engaging comprise two friction wheels mounted against said opposite first and second flat faces, a first friction wheel driven by said torsion cable, to turn at the same angular speed as said torsion cable, said second friction wheel being driven by a concentrically mounted follower device maintained in motion by a command device turned by said torsion cable, said follower device and said command device turning at same angular speed.

11. A power operated saw as defined in claim 7 wherein said means for mounting said blade comprise a set of three flanged guide bearings 60 in contact against said inner edge, two of said flanged guide bearings 60 having each a fixed central axis and having between each other a cutting area 63 to permit passage of a piece to work on, the third flanged guide bearing 60 being mounted on a spring arm located on said fore end and being biased towards said inner edge.

12. A power operated saw as defined in claim 9 further comprising means for control of said electric motor comprising a conduit and a pressure switch to apply various speeds.

13. A flexible drive cable operated saw machine for cutting materials through a solid element, said drive cable operated saw machine comprising in combination:

a main body 22 having a force end and a aft end, a rotating axis 72 and being capable of being oriented about said rotating axis, an annular cutting blade 54 comprising an outer edge, a first flat face and a second flat face opposite to said first flat face and an inner edge, said outer edge comprising cutting means disposed along the perimeter thereof, said annular cutting blade 54 being mounted on said force end of said main body, wherein said annular cutting blade is engaged into rotation against said solid element by a command wheel centrally mounted on said drive cable and peripherally exerting a friction drive against said first flat face, said drive cable also engaging a command gear meshing with a follower gear of identical diameter, said follower gear driving a follower wheel acting on said second flat face of said annular cutting blade 54 in transverse register with said command wheel relative to said cutting blade, said cutting means having a diameter and a thickness, wherein said diameter comprising an outside diameter at said outer edge and an inside diameter at said inner edge, said flat faces having a width corresponding to half of the difference between said inside diameter being no less than 75% of said outside diameter and no more tan 97% of said outside diameter, said thickness relative to said diameter being in a ratio varying from 0.5 to 1 000, to 3 to 1 000.

* * * * *